(12) United States Patent
Nauber et al.

(10) Patent No.: US 10,969,361 B2
(45) Date of Patent: *Apr. 6, 2021

(54) ELECTROCHEMICAL GAS SENSOR, LIQUID ELECTROLYTE AND USE OF A LIQUID ELECTROLYTE IN AN ELECTROCHEMICAL GAS SENSOR

(71) Applicant: Dräger Safety AG & Co. KGaA, Lübeck (DE)

(72) Inventors: Andreas Nauber, Stockelsdorf (DE); Michael Sick, Timmendorfer Strand (DE); Gregor Steiner, Titisee-Neustadt (DE); Marie-Isabell Mattern-Frühwald, Bargteheide (DE); Frank Mett, Lübeck (DE); Rigobert Chrzan, Bad Oldesloe (DE); Sabrina Pilz, Lübeck (DE)

(73) Assignee: Dräger Safety AG & Co. KGaA, Lübeck (DE)

(*) Notice: Subject to any disclaimer, the term of this patent is extended or adjusted under 35 U.S.C. 154(b) by 260 days.

This patent is subject to a terminal disclaimer.

(21) Appl. No.: 16/206,032

(22) Filed: Nov. 30, 2018

(65) Prior Publication Data

US 2019/0101506 A1   Apr. 4, 2019

Related U.S. Application Data

(62) Division of application No. 14/889,968, filed as application No. PCT/EP2014/002363 on Sep. 1, 2014, now Pat. No. 10,175,191.

(30) Foreign Application Priority Data

Sep. 9, 2013   (DE) .................... 10 2013 014 994.0

(51) Int. Cl.
  *G01N 27/404*   (2006.01)
  *H01G 11/58*    (2013.01)
  (Continued)

(52) U.S. Cl.
  CPC ....... *G01N 27/4045* (2013.01); *G01N 27/301* (2013.01); *G01N 27/413* (2013.01);
  (Continued)

(58) Field of Classification Search
  CPC .................. H01G 9/035; H01G 11/58; H01M 2300/0002; H01M 2300/0005; H01M 2300/00111; G01N 27/404; G01N 27/4045
  See application file for complete search history.

(56) References Cited

PUBLICATIONS

Ji et al., "Electrode Kinetic Studies of the Hydroquinone-Benzoquinone System and the Reaction between Hydroquinone and Ammonia in Propylene Carbonate: Application to the Indirect Electroanalytical Sensing of Ammonia," J. Phys. Chem. C 2007, 111, 1496-1504 with Suporting Information (Year: 2007).*

* cited by examiner

*Primary Examiner* — Alexander S Noguerola
(74) *Attorney, Agent, or Firm* — McGlew and Tuttle, P.C.

(57) ABSTRACT

An electrochemical gas sensor (10) has a housing (20), a working electrode (51), a counterelectrode (52) and a reference electrode (53). The housing (20) has an electrolyte reservoir (30), a gas inlet orifice (21) and at least one gas outlet orifice (22). The electrolyte reservoir (30) is filled with a liquid electrolyte (40). The gas sensor (10) has a counterelectrode carrier (26). The counterelectrode (52) is suspended on the counterelectrode carrier (26) in such a way that the counterelectrode (52) is suspended in the electrolyte reservoir (30) and the electrolyte (40) flows around the counterelectrode (52) on all sides. Preferably, the electrolyte includes (I) a solvent, e.g. water, propylene carbonate, (Continued)

ethylene carbonate or mixtures thereof; (ii) a conductive salt, especially an ionic liquid; and/or (iii) an organic mediator, for example substituted quinones, anthraquinones, etc.

18 Claims, 4 Drawing Sheets

(51) Int. Cl.
*G01N 27/30* (2006.01)
*G01N 27/413* (2006.01)
*G01N 33/00* (2006.01)
*H01G 9/035* (2006.01)

(52) U.S. Cl.
CPC ......... *G01N 33/0054* (2013.01); *H01G 9/035* (2013.01); *H01G 11/58* (2013.01); *H01M 2300/0011* (2013.01); *Y02A 50/20* (2018.01)

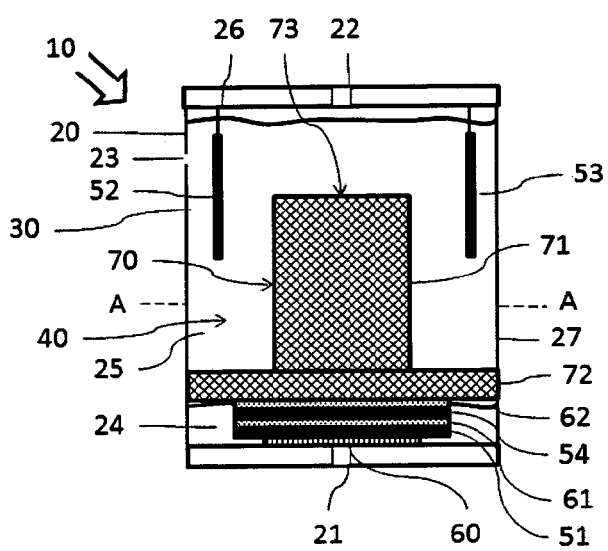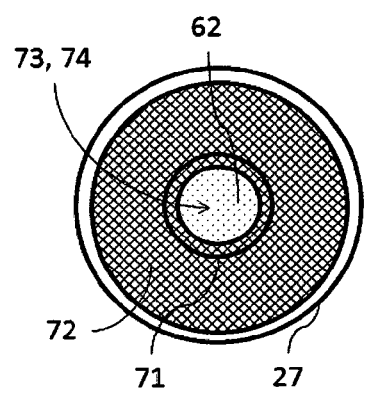
Fig. 2a
Fig. 2b

ELECTROCHEMICAL GAS SENSOR, LIQUID ELECTROLYTE AND USE OF A LIQUID ELECTROLYTE IN AN ELECTROCHEMICAL GAS SENSOR

CROSS REFERENCE TO RELATED APPLICATIONS

This application is a divisional under 37 CFR 1.53(b) of pending prior U.S. application Ser. No. 14/889,968 filed Nov. 9, 2015 and claims the benefit (35 U.S.C. § 120 and 365(c)) of International Application PCT/EP2014/002363 filed Sep. 1, 2014, which designated inter alia the United States and which claims the priority of German patent application number 10 2013 014 994.0 filed Sep. 9, 2013, the entire contents of each application are incorporated herein by reference.

FIELD OF THE INVENTION

The present invention pertains to an electrochemical gas sensor, a liquid electrolyte for an electrochemical gas sensor as well as to the use of such a liquid electrolyte in an electrochemical gas sensor, to the use of an electrochemical gas sensor for detecting $NH_3$ or $NH_3$-containing gas mixtures, and to the use of a liquid electrolyte for detecting $NH_3$ or $NH_3$-containing gas mixtures.

BACKGROUND OF THE INVENTION

Electrochemical gas sensors, with which the concentration of gaseous nitrogen compounds can be detected over a limited time period, are generally known. Such sensors are usually used in a great variety of industrial areas, ranging from the chemical industry to agricultural plants via the monitoring of refrigerating systems. They are used especially to recognize critical concentrations of flammable and/or toxic gases in time and to warn of a corresponding hazard. In particular, the monitoring of the concentration of ammonia ($NH_3$), hydrazine and amines is of interest in this connection. Such electrochemical sensors usually comprise a plurality of electrodes, which are in conductive contact with an electrolyte liquid and form in this way a galvanic cell, hereinafter also called measuring cell.

EP 0 395 927 B1 discloses, for example, an electrochemical measuring cell for determining ammonia or hydrazine in a gaseous or liquid test sample, with at least one measuring electrode and a counterelectrode. To generate a reference potential for the determination of ammonia or hydrazine, a reference electrode, whose potential is used as a reference point for the measurement, is inserted into this measuring cell. EP 0 556 558 B1 also discloses such electrochemical measuring cells for determining ammonia, amines, hydrazine and hydrazine derivatives.

The detection of nitrogen-containing compounds, e.g., ammonia, different amines or hydrazine, is typically carried out in such measuring cells by means of an electrochemical reaction between the gas flowing into the sensor, the electrodes and the electrolyte of the sensor. For example, ammonia flowing in can be oxidized at a first electrode (typically called working electrode) Ammonium ions can be formed in the process, and they will diffuse to a second electrode (typically called counterelectrode). The ammonium ions can again be deprotonated there. This reaction leads to a detectable flow of current in the galvanic cell. The flow of current thus indicates the presence of the gas to be detected (hereinafter also called "reactive species").

However, various problems may arise in such prior-art electrochemical measuring cells. Thus, not only ammonium ions, but also additional nitrogen compounds may be formed in the above-described reaction. However, these may become deposited on the electrodes and make difficult in this way the reaction of additional ammonia molecules or other molecules to be detected, which enter the sensor, and even block the reaction nearly completely. One also speaks of poisoning of the sensor (sensor poisoning) in this connection. Such a sensor poisoning may cause, on the one hand, an impairment of the basic measuring sensitivity of the sensor, and, on the other hand, the signal stability may decrease markedly in case of continuous gas admission. The sensitivity of the sensor may decrease further with each detection of gaseous ammonia, until reliable measurement will finally become impossible. In addition, changes of the zero signal in case of a change in the ambient humidity and the cross sensitivity to other gases may also be problematic.

SUMMARY OF THE INVENTION

Based on this, an object of the present invention is to overcome these and further drawbacks of the state of the art and to provide an improved electrochemical gas sensor. In particular, a gas sensor shall be provided, which has the highest possible measuring sensitivity, the best possible signal stability under permanent load and/or a cross sensitivity that is reduced as much as possible. Furthermore, the gas sensor shall be able to be manufactured in the most cost-effective and simple manner possible.

In an electrochemical gas sensor with a housing, with a working electrode, with a counterelectrode and with a reference electrode, wherein the housing has an electrolyte reservoir, a gas inlet opening and at least one gas outlet opening, and the electrolyte reservoir is filled with a liquid electrolyte, the present invention makes provisions for the gas sensor to have a counterelectrode carrier, wherein the counterelectrode is suspended on the counterelectrode carrier such that the counterelectrode is suspended on the counterelectrode carrier and the electrolyte flows around the counterelectrode on all sides.

It is of great advantage in such a sensor that the gas sensor has a counterelectrode carrier, on which the counterelectrode is suspended. The electrolyte can thus flow in this way around the counterelectrode from all sides. On the one hand, ions diffusing to the counterelectrode, which are formed during the reaction of the reactive species at the working electrode, for example, ammonium ions, can reach the counterelectrode freely through the electrolyte. On the other hand, reactive species formed by the reverse reaction taking place at the counterelectrode, for example, ammonia molecules, or other reaction products can also be removed from the counterelectrode. It is also advantageous in this connection that the electrochemical gas sensor has a gas outlet opening. The gas to be detected can thus be released again from the gas sensor in a simple manner after the reverse reaction has taken place at the counterelectrode. An additional opening may also be present in the lateral housing wall for the additional pressure equalization. The gas formed at the counterelectrode can therefore escape through the gas outlet opening and through the additional opening, so that neither will a poisoning of the counterelectrode occur, nor will an undesired overpressure develop in the sensor.

It is therefore seen that the counterelectrode is preferably not a gas diffusion electrode. The counterelectrode may rather be, for example, a wire-shaped electrode, which can be suspended into the electrolyte from the counterelectrode carrier.

The working electrode is preferably a gas diffusion electrode, which is arranged in the housing behind the gas inlet opening. It is favorable, for example, if the working electrode is arranged in the housing such that the gas flowing in through the gas inlet will reach the working electrode directly. It is conceivable in this connection that a protective membrane, which prevents the working electrode from being able to be damaged mechanically, e.g., by dust particles, is arranged between the gas inlet and the working electrode.

The working electrode may be, for example, a coated PTFE membrane. The coating may be, for example, a coating consisting of carbon nanotubes. However, it is also conceivable that the working electrode consists of a noble metal or a noble metal mixture. It is thus conceivable, among other things, that the working electrode is a carbon electrode, preferably an electrode consisting of single-walled carbon nanotubes, multiwalled carbon nanotubes or surface-active carbon, or an iridium sputter electrode. For example, the working electrode may also be a PTFE membrane, which was sputtered with iridium or another metal.

The counterelectrode advantageously consists entirely or partially of single-walled carbon nanotubes, multiwalled carbon nanotubes, surface-active carbons, ruthenium, iridium, platinum, palladium, gold or mixtures of ruthenium, iridium, platinum, palladium and/or gold. The working electrode and/or the counterelectrode may consist of noble metal, noble metal mixture or carbon. The working electrode and the counterelectrode may consist of the same material in this connection. As an alternative, the working electrode and the counterelectrode may also consist of different materials.

It is advantageous in a preferred embodiment if the gas sensor has a separating element, which divides the housing into an upper chamber and a lower chamber. Electrodes are arranged in both the upper chamber and the lower chamber. It is therefore favorable if electrolyte is present in both the upper chamber and the lower chamber. The upper chamber and the lower chamber are preferably connected fluidically to one another, so that an exchange can take place between the electrolyte in the upper chamber and the electrolyte in the lower chamber.

It is especially advantageous if the upper chamber forms the electrolyte reservoir. It is therefore meaningful if the counterelectrode is arranged in the upper chamber. The working electrode is, for example, a gas diffusion electrode in this case as well, which is arranged, as described above, in the housing behind the gas inlet opening. It is favorable in this connection if the working electrode is arranged in the lower chamber. An intermediate membrane may be arranged between the working electrode and the separating element. The intermediate membrane can protect, on the one hand, the working electrode from damage due to a direct contact with the separating element. This is meaningful, for example, if the separating element is used not only to divide the housing into two chambers, but also to press the working electrode in the lower chamber in the direction of the gas inlet. On the other hand, the intermediate membrane may be used to guide the electrolyte from the upper chamber into the lower chamber. For example, the electrolyte may be able to be guided through an opening in the separating element from the upper chamber into the lower chamber. The intermediate membrane can then ensure a certain minimum distance between the separating element and the electrode arranged under it. The intermediate membrane is preferably designed such that it is permeable to the electrolyte. At the same time, the intermediate membrane favorably has such a dimensional stability that it can guarantee a certain minimum distance between the components between which it is arranged. For example, the intermediate membrane may be a glass fiber membrane. The electrolyte, which flows through the separating element from the upper chamber to the lower chamber, can enter the lower chamber through the intermediate membrane in this way. Electrolytes can thus always flow around the working electrode on all sides. In addition, a fluid contact can thus always be present between the electrolyte in the upper chamber and in the lower chamber. A conductive contact can always be present in this way between the working electrode and the counterelectrode especially by means of the electrolyte. This is especially advantageous if the working electrode is arranged in the lower chamber and the counterelectrode, as was described above, in the upper chamber. If is thus seen in this connection that it is advantageous if the separating element is configured such that electrolyte can be guided through the separating element from the upper chamber into the lower chamber.

It is conceivable in this connection if the separating element consists of a material that is basically permeable to the electrolyte. The separating element may be used in this case especially to guarantee a certain minimum distance between the working electrode arranged in the lower chamber and the counterelectrode arranged in the upper chamber. The separating element may be configured for this in such a way that it presses the working electrodes in the direction of the gas inlet as much as possible.

It is also conceivable in a preferred embodiment that the separating element consists basically of a material not permeable to the electrolyte. For example, a passage opening, which is used to exchange electrolyte between the upper and lower chambers, may be formed in the separating element in this case. The passage opening may be, for example, a passage channel.

It is preferable, for example, if the separating element has at least one top part and one foot part. The foot part may be used to separate the upper chamber from the lower chamber. Furthermore, the foot part can fix the working electrode and—if present—the intermediate membrane arranged between the separating element and the working electrode in the direction of the gas inlet in the housing. The top part may be configured, for example, in the manner of a wick and used to guide the electrolyte from the upper chamber into the lower chamber. For example, the top part may have the shape of a tube. This tube preferably has an upper opening and a lower opening. The tube is arranged on the foot part, for example, such that the upper opening is open towards the upper chamber and the lower opening of the tube corresponds to an opening in the foot part. The electrolyte from the upper chamber can in this way enter the tube through the upper opening and from there the lower chamber through the lower opening. It can be ensured in this way that there is a fluid connection between the upper chamber and the lower chamber.

It is also conceivable that the counterelectrode carrier is part of the separating element. For example, the counterelectrode carrier may be arranged on the top part of the separating element. It is seen that the counterelectrode is preferably arranged in the upper chamber.

It is advantageous in another preferred embodiment if the gas sensor has, moreover, a collecting electrode. Such a collecting electrode can prevent an excess of the reactive species to be detected from diffusing into the upper chamber in an uncontrolled manner. The collecting electrode is preferably arranged between the working electrode and the separating element.

In this connection an intermediate membrane may also be arranged between the working electrode and the collecting electrode. Such an intermediate membrane preferably consists of a material permeable to the electrolyte, which is dimensionally stable to a certain extent, for example, a glass fiber membrane, in this case as well. The collecting electrode and the working electrode may be arranged in this way such that they are not in direct contact with one another, but there is at the same time an electrically conductive contact through the electrolyte, which impregnates the intermediate membrane. The distance between the working electrode and the collecting electrode can be selected to be relatively short by means of this intermediate membrane and is determined only by the thickness of the intermediate membrane.

An intermediate membrane may also be arranged between the collecting electrode and the separating element. This intermediate membrane will act as the intermediate membrane already described above, which is arranged—in case of a collecting electrode being absent—between the working electrode and the separating element.

It is seen that an electrochemical gas sensor according to the present invention may be configured, for example, such that it has a housing, which is divided by means of a separating element into an upper chamber and a lower chamber. The upper chamber may act as an electrolyte reservoir. The upper and lower chambers of the housing may be filled with a liquid electrolyte. The separating element is preferably configured such that the electrolyte can flow through the separating element from the upper chamber into the lower chamber.

A gas inlet may be formed in the lower chamber and a gas outlet in the upper chamber. Furthermore, an additional opening may be formed in the upper chamber for pressure equalization. The gas to be detected, i.e., the reactive species, can flow into the housing through the gas inlet.

The working electrode of the gas sensor according to the present invention is preferably arranged behind the gas inlet in the lower chamber in the direction of flow. A protective membrane is favorably formed between the gas inlet and the working electrode. Furthermore, a collecting electrode may be preferably formed in the lower chamber. The working electrode and the collecting electrode may be separated from each other by an intermediate membrane, for example, a glass fiber membrane. An additional intermediate membrane is preferably formed between the collecting electrode and the separating element. If no collecting electrode is present, an intermediate membrane may also be formed between the working electrode and the separating element. It is seen that it is favorable if a gas sensor according to the present invention has at least one intermediate membrane between the working electrode and the separating element. A gas sensor according to the present invention preferably has a first intermediate membrane between the working electrode and the collecting electrode and a second intermediate membrane between the collecting electrode and the separating element.

The counterelectrode is preferably arranged in the upper chamber, i.e., the electrolyte reservoir, in such a gas sensor according to the present invention. The gas sensor has a counterelectrode carrier here, to which the counterelectrode is fastened. The counterelectrode carrier is preferably part of the separating element configured as was described above.

It is advantageous, furthermore, if the reference electrode is arranged in the electrolyte reservoir and the electrolyte flows around it on all sides. It is favorable if the reference electrode is suspended on the counterelectrode carrier. The reference electrode can be located in this way at the greatest possible distance from the other electrodes but at the same time detect the conditions in the sensor effectively and accurately.

To detect reactive species, which include, for example, amine compounds, ammonia or hydrazine, it is especially advantageous if the electrolyte contains at least one solvent, a conductive salt and/or an organic mediator.

It is favorable in any case if the solvent is selected from the group comprising water and alkylene carbonate or mixtures thereof, preferably selected from the group containing water, propylene carbonate, ethylene carbonate or mixtures thereof. A mixture of propylene carbonate and ethylene carbonate proved to be especially favorable. It is favorable, furthermore, if the conductive salt is an ionic liquid, an inorganic salt or a mixture of an ionic liquid and an inorganic salt, the anion being preferably selected from the group containing halides, carbonate, sulfonate, phosphate and/or phosphonate, and wherein the cation is preferably selected from the group containing metal ions, onium ions or a mixture of metal ions and onium ions. The term onium ions is defined as cations that can be formally obtained by the protonation of a mononuclear starting hydride of elements of the nitrogen, carbon or halogen group.

It is favorable, furthermore, if the organic mediator has a quinoid system, preferably selected from the group containing ortho-quinones, para-quinones, substituted ortho-quinones and substituted para-quinones, dihydroxynaphthalene, substituted dihydroxynaphthalene, anthraquinone, substituted anthraquinone, especially preferably selected from the group containing 1,2-dihydroxybenzene, 1,4-dihydroxybenzene, 1,4-naphthohydroquinone, substituted 1,2-dihydroxybenzene, substituted 1,4-dihydroxybenzene, substituted 1,4-naphthohydroquinone, especially preferably selected from the group containing substituted anthraquinone, substituted 1,2-dihydroxybenzene and substituted 1,4-dihydroxybenzene. The organic mediator is especially preferably a dihydroxybenzene compound, which can be oxidized into a quinone compound at the working electrode. Gas flowing simultaneously into the sensor, e.g., ammonia, an amine compound or even hydrazine, can be reduced. The quinone compound formed can again be reduced to the dihydroxybenzene compound in the course of the opposing reaction taking place at the counterelectrode, and the gas, for example, ammonium ions formed in the direct reaction, can again be oxidized into its starting state and subsequently released through the gas outlet of the sensor. If the dihydroxybenzene compound is, for example, 1,2-dihydroxybenzene, the following two reactions can take place at the working electrode:

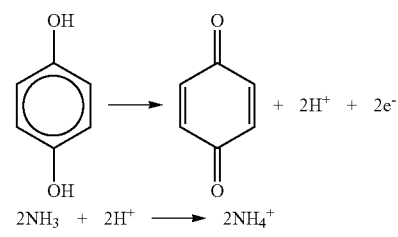

The two reverse reactions, namely,

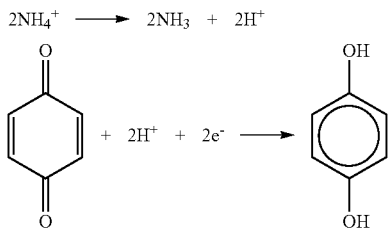

can then take place at the counterelectrode.

A pH gradient may develop between the working electrode and the counterelectrode in connection with these reactions. It is seen that it is therefore favorable if the electrolyte contains a buffer, said buffer preferably being a compound corresponding to

in which n=1, 2, 3, 4 or 5, preferably n=2 or n=3, wherein all $R^2$ and $R^3$ are selected, independently from one another, from among H, NH and OH, and wherein $R^1$ is selected from the group containing piperazinyl, substituted piperazinyl, N-morpholino, cycloalkyl, tris-(hydroxyalkyl)alkyl. Such a buffer, especially preferably a buffer in which N-morpholino is selected as $R^1$, especially 3-(N-morpholino)propanesulfonic acid or another 3-(N-morpholino)-alkanesulfonic acid, can be favorably used to stabilize the pH value of the reaction solution.

It is therefore seen that it is favorable if the electrolyte is composed of
a. a solvent, which is selected from among water, propylene carbonate, ethylene carbonate or mixtures thereof,
b. a conductive salt, which is selected from among 1-hexyl-3-methylimidazolium-tris(pentafluoroethyl)trifluorophosphate or tetraalkylammonium toluene sulfate,
c. an organic mediator, which is selected from the group containing substituted anthraquinone, substituted 1,2-hydroquinone, substituted 1,4-hydroquinone, especially preferably tert-butylhydroquinone or anthraquinone-2-sulfonic acid,
d. optionally a buffer, which is selected from among 3-(N-morpholino)-propanesulfonic acid or 3-(N-morpholino)-ethanesulfonic acid, and
e. optionally a compound lowering the freezing point of the composition, selected from the group containing propylene glycol and ethylene glycol.

A preferred embodiment of an electrochemical gas sensor according to the present invention may thus be an electrochemical gas sensor with a housing, a working electrode, a counterelectrode and a reference electrode, wherein the housing has an electrolyte reservoir, a gas inlet opening and at least one gas outlet opening, and the electrolyte reservoir is filled with a liquid electrolyte, wherein the electrolyte contains at least one solvent, a conductive salt and/or an organic mediator and wherein the electrolyte is composed of
a. a solvent, which is selected from among water, propylene carbonate, ethylene carbonate or mixtures thereof,
b. a conductive salt, which is selected from among 1-hexyl-3-methylimidazolium-tris(pentafluoroethyl)trifluorophosphate or tetraalkylammonium toluene sulfate,
c. an organic mediator, which is selected from the group containing substituted anthraquinone, substituted 1,2-hydroquinone, substituted 1,4-hydroquinone, especially preferably substituted tert-butylhydroquinone or anthraquinone-2-sulfonic acid,
d. optionally a buffer, which is selected from among 3-(N-morpholino)-propanesulfonic acid or 3-(N-morpholino)-ethanesulfonic acid, and
e. optionally a compound lowering the freezing point of the composition, selected from the group containing propylene glycol and ethylene glycol.

For example, an electrochemical gas sensor may comprises a housing, a working electrode, a counterelectrode and a reference electrode, wherein the housing has an electrolyte reservoir, a gas inlet opening and at least one gas outlet opening, and the electrolyte reservoir is filled with a liquid electrolyte, wherein the electrolyte contains at least one solvent, a conductive salt and/or an organic mediator and wherein the electrolyte is a composition comprising a solvent, which is a mixture of propylene carbonate and ethylene carbonate, 1-hexyl-3-methylimidazolium-tris(pentafluoroethyl)-trifluorophosphate as a conductive salt, tert-butyl-1,2-dihydroxybenzene or anthraquinone-2-sulfonic acid as an organic mediator, as well as 3-(N-morpholino)-propanesulfonic acid as a buffer. It is especially advantageous in such a gas sensor if the gas sensor has a counterelectrode carrier, wherein the counterelectrode is suspended on the counterelectrode carrier such that it is suspended in the electrolyte reservoir and the electrolyte flows around it on all sides.

It is therefore seen that it is favorable in a liquid electrode for an electrochemical gas sensor, especially for an electrochemical gas sensor that is suitable for detecting $NH_3$ or $NH_3$-containing gas mixtures if the electrolyte contains at least one solvent, a conductive salt and/or an organic mediator, wherein the conductive salt is an ionic liquid, an inorganic salt, an organic salt or a mixture thereof.

Such an electrolyte can be used with great advantage especially for electrochemical gas sensors in which electrodes made of noble metal or carbon nanotubes are used in order to improve the resistance of such a sensor to continuous gas admission. In particular, the risk of a poisoning, as was described above, can be markedly minimized in this way.

It is especially advantageous here if the electrolyte contains a buffer, the buffer preferably being a compound corresponding to

in which n=1, 2, 3, 4 or 5, preferably n=2 or n=3, wherein all $R^2$ and $R^3$ are selected, independently from one another, from among H, NH or OH, and wherein $R^1$ is selected from the group containing piperazinyl, substituted piperazinyl, N-morpholino, cycloalkyl, and tris-(hydroxyalkyl)alkyl. For example, $R^2$ and $R^3$ may be selected independently from one another from among H, NH and OH, wherein n=2 and $R^1$ is selected from the group containing piperazinyl, substituted piperazinyl, N-morpholino, cycloalkyl and tris-(hydroxyalkyl)alkyl. $R^2$ and $R^3$ may be selected independently from one another from among H, NH and OH, wherein n=2 and $R^1$ is selected from the group containing N-morpholino and tris-(hydroxyalkyl)alkyl. For example, it is especially advantageous here if n=2 or n=3, and all $R^2$ and $R^3$ are selected, independently from one another, from among H, NH and OH, and wherein $R^1$ is selected from among [4-(2-hydroxyethyl)-1]-piperazinyl, (N-morpholino), N-cyclohexyl and tris-(hydroxymethyl)methyl. The buffer is especially preferably 3-(N-morpholino)-propanesulfonic acid or 3-(N-morpholino)-ethanesulfonic acid. The electrolyte may be a mixture of a solvent, a conductive salt and/or an organic mediator, wherein the conductive salt is an ionic liquid, an inorganic salt, an organic salt or a mixture thereof and wherein the electrolyte contains, moreover, a buffer, especially a buffer that is selected from among 3-(N-morpholino)-propanesulfonic acid or 3-(N-morpholino)-ethanesulfonic acid.

To prevent the electrolyte from drying out after a certain time, e.g., if the sensor shall be used in continuous operation, it is advantageous, moreover, if the electrolyte contains a component for lowering the vapor pressure as an additional component. The additional component may preferably be an alkylene glycol or polyalkylene glycol, and it is especially preferably propylene glycol, ethylene glycol or a mixture of propylene glycol and ethylene glycol. The electrolyte may be a mixture of a solvent, a conductive salt and/or an organic mediator, wherein the conductive salt is an ionic liquid, an inorganic salt, an organic salt or a mixture thereof, and wherein the electrolyte contains, moreover, at least one alkylene glycol, especially an alkylene glycol, which is selected from among propylene glycol, ethylene glycol or a mixture of propylene glycol and ethylene glycol.

It is favorable, furthermore, if the solvent is selected from the group containing water and alkylene carbonate or mixtures thereof, preferably selected from the group containing water, propylene carbonate, ethylene carbonate or mixtures thereof. The electrolyte may be a mixture of a solvent, a conductive salt and/or an organic mediator, wherein the conductive salt is an ionic liquid, an inorganic salt, an organic salt or a mixture thereof and wherein the solvent is water. As an alternative the electrolyte may be a mixture of a solvent, a conductive salt and/or an organic mediator, wherein the conductive salt is an ionic liquid, an inorganic salt, an organic salt or a mixture thereof and wherein the solvent is alkylene carbonate, especially propylene carbonate, ethylene carbonate or a mixture of propylene carbonate and ethylene carbonate. In this connection, in particular, the electrolyte may be a mixture of a solvent, a conductive salt and/or an organic mediator, wherein the conductive salt is an ionic liquid, an inorganic salt, an organic salt or a mixture thereof, wherein the electrolyte also contains, moreover, a buffer especially a buffer that is selected from among 3-(N-morpholino)-propanesulfonic acid or 3-(N-morpholino)-ethanesulfonic acid and wherein the solvent is alkylene carbonate, especially propylene carbonate, ethylene carbonate or a mixture of propylene carbonate and ethylene carbonate. The electrolyte may be a mixture of a solvent, a conductive slat and/or an organic mediator, wherein the conductive salt is an ionic liquid, an inorganic salt, an organic salt or a mixture thereof, wherein the electrolyte contains, moreover, at least one alkylene glycol, especially an alkylene glycol, which is selected from among propylene glycol, ethylene glycol or a mixture of propylene glycol and ethylene glycol, and wherein the solvent is alkylene carbonate, especially propylene carbonate, ethylene carbonate or a mixture of propylene carbonate and ethylene carbonate.

The anion of the conductive salt is preferably selected from the group containing halides, carbonate, sulfonate, phosphate and/or phosphonate, preferably an anion selected from the group containing alkyl sulfonate, alkenyl sulfonate, aryl sulfonate, alkyl phosphate, alkenyl phosphate, aryl phosphate, substituted alkyl sulfonate, substituted alkenyl sulfonate, substituted aryl sulfonate, substituted alkyl phosphate, substituted alkenyl phosphate, substituted aryl phosphate, halogenated phosphate, halogenated sulfonate, halogenated alkyl sulfonate, halogenated alkenyl sulfonate, halogenated aryl sulfonate, halogenated alkyl phosphate, halogenated alkenyl phosphate, halogenated aryl phosphate, especially preferably an anion selected from the group containing fluorophosphate, alkyl fluorophosphate, aryl sulfonate, and especially preferably from the group containing perfluoroalkyl fluorophosphate and toluene sulfonate.

It is advantageous if the conductive salt contains metal ions, onium ions or mixture of metal ions and onium ions as cations. For example, the metal ions may be selected from among alkali metal ions or alkaline earth metal ions, preferably from among Li, K and/or Na. It is favorable if the onium ions are selected from among ammonium, phosphonium, guanidinium cations and heterocyclic cations, preferably selected from among alkylammonium and heterocyclic cations, especially preferably selected from among alkylammonium, imidazolium and/or substituted imidazolium ions, wherein the substituted imidazolium ions preferably have a structure corresponding to

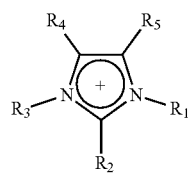

Formula II wherein $R_1$, $R_2$, $R_3$, $R_4$ and $R_5$ may be selected, independently from one another, from among —H, straight-chain or branched alkyl containing 1 to 20 C atoms, straight-chain or branched alkenyl containing 2 to 20 C atoms and one or more double bonds, straight-chain or branched alkinyl containing 2 to 20 C atoms and one or more triple bonds, saturated, partially or fully unsaturated cycloalkyl containing 3-7 C atoms, which may be substituted with alkyl groups containing 1 to 6 C atoms, saturated, partially or fully unsaturated heteroaryl, heteroaryl-C1-C6-alkyl or aryl-C1-C6-alkyl, wherein $R_2$, $R_4$ and $R_5$ are especially preferably H, and $R_1$ and $R_3$ represent each, independently from one another, a straight-chain or branched alkyl containing 1 to 20 C atoms.

Tetrabutyl ammonium toluene sulfonate or 1-hexyl-3-methylimidazolium-tris(pentafluoroethyl)-trifluorophosphate may be used as the conductive salt. As an alternative the conductive salt may be, for example, LiCl, KCl or a mixture of LiCl and KCl. It is thus especially advantageous if the electrolyte is a mixture of a solvent, a conductive salt and/or an organic mediator, wherein the conductive salt is selected from among LiCl, KCl, alkylammonium toluene sulfonate and ionic liquids, with a perfluoroalkyl fluorophosphate anion.

It is favorable, furthermore, if the organic mediator is a polyhydroxy compound, which forms a quinoid system or a naphthalene system during oxidation. For example, the inorganic mediator may be selected from the group containing ortho-dihydroxybenzene, para-dihydroxybenzene, substituted ortho-dihydroxybenzenes and substituted para-dihydroxybenzenes, dihydroxynaphthalene, substituted dihydroxynaphthalene, anthrahydroquinone, substituted anthrahydroquinone, preferably 1,2-dihydroxybenzene, 1,4-dihydroxybenzene, naphthohydroquinone, substituted 1,2- or 1,4-dihydroxybenzene, substituted hydroquinone, substituted naphthohydroquinone, especially preferably substituted anthrahydroquinone, substituted hydroquinone, and substituted 1,2-dihydroxybenzene. It is especially favorable in this connection if the substituents of the substituted anthraquinone, substituted 1,2-dihydroxybenzene and/or substituted 1,4-hydroquinone are selected from the group containing sulfonyl, tert-butyl, hydroxyl, alkyl, aryl, preferably sulfonic acid and/or tert-butyl.

It is especially favorable in any case if the electrolyte contains a mixture of propylene carbonate and/or ethylene carbonate as the solvent, LiCl, KCl, tetrabutylammonium toluene sulfonate and/or 1-hexyl-3-methyl-imidazolium tris (pentafluoroethyl)-trifluorophosphate or a mixture of two or more of these components as the conductive salt and tert-butylhydroquinone and/or a substituted anthraquinone, preferably anthraquinone-2-sulfonate as organic mediator.

The concentration of the organic mediator may be between $10^{-6}$ mol/L and $10^{-2}$ mol/L. Thus, the organic mediator may be contained in the electrolyte at a concentration of $10^{-2}$ mol/L or less, preferably $10^{-3}$ mol/L or less, especially preferably $5 \cdot 10^{-4}$ mol/L or less, especially preferably $2 \cdot 10^{-4}$ mol/L or less. The organic mediator may be contained in the electrolyte at a concentration of $10^{-6}$ mol/L or more, preferably $10^{-5}$ mol/L or more, especially preferably $5 \cdot 10^{-5}$ mol/L or more, especially preferably $8 \cdot 10^{-5}$ mol/L or more, and especially preferably $10^{-4}$ mol/L or more. The organic mediator may be present at a concentration of $10^{-5}$ mol/L to $10^{-3}$ mol/L, preferably $5 \cdot 10^{-5}$ mol/L to $5 \cdot 10^{-4}$ mol/L, especially preferably $8 \cdot 10^{-5}$ mol/L to $2 \cdot 10^{-4}$ mol/L, and especially preferably $10^{-4}$ mol/L.

Therefore, the present invention pertains, in another aspect, to a liquid electrolyte for an electrochemical gas sensor corresponding to at least one of the above claims, wherein the electrolyte contains at least one conductive salt, a solvent and an organic mediator, wherein the electrolyte also contains a buffer, wherein the buffer is preferably a compound corresponding to

$$R^1\text{—}(CR^2R^3)_n\text{—}SO_3H, \quad (I)$$

in which n=1, 2, 3, 4 or 5, preferably n=2 or n=3, wherein all $R^2$ and $R^3$ are selected, independently from one another, from among H, NH and OH, and wherein $R^1$ is selected from the group containing piperazinyl, substituted piperazinyl, N-morpholino, cycloalkyl, tris-(hydroxyalkyl)alkyl, wherein the conductive salt contains an ionic liquid and wherein the solvent is selected from among water, propylene carbonate, ethylene carbonate or mixtures thereof. The organic mediator is preferably selected here from the group containing ortho-quinones, para-quinones, substituted ortho-quinones and substituted para-quinones, dihydroxynaphthalene, substituted dihydroxynaphthalene, anthraquinone, and substituted anthraquinone, preferably 1,2-dihydroxybenzene, 1,4-dihydroxybenzene, 1,4-naphthodihydroxybenzene, substituted 1,2-dihydroxybenzene, substituted 1,4-dihydroxybenzene, substituted 1,4-naphthodihydroxybenzene, especially preferably substituted anthraquinone, substituted 1,2-dihydroxybenzene, and substituted 1,4-dihydroxybenzene, wherein the substituents of the substituted anthraquinone, substituted 1,2-hydroquinone and/or substituted 1,4-hydroquinone are selected from the group containing sulfonyl, tert-butyl, hydroxyl, alkyl, aryl, preferably sulfonic acid and tert-butyl.

Furthermore, the buffer is preferably a compound corresponding to

$$R^1\text{—}(CR^2R^3)_n\text{—}SO_3H, \quad (I)$$

in which n=1, 2, 3, 4 or 5, preferably n=2 or n=3, wherein all $R^2$ and $R^3$ are selected, independently from one another, from among H, NH and OH, and wherein $R^1$ is selected from the group containing piperazinyl, substituted piperazinyl, N-morpholino, cycloalkyl, tris-(hydroxyalkyl)alkyl, wherein the buffer is preferably a compound corresponding to Formula I, with n=2 or n=3, wherein all $R^2$ and $R^3$ are selected, independently from one another, from among H, NH and OH, and wherein $R^1$ is selected from among [4-(2-hydroxyethyl)-1]-piperazinyl, (N-morpholino)-, N-cyclohexyl-, tris-(hydroxymethyl)methyl, wherein the buffer is especially preferably 3-(N-morpholino)-propanesulfonic acid.

It is seen that it is especially advantageous to use a liquid electrolyte according to the present invention in an electrochemical gas sensor according to the present invention. The use of an electrochemical gas sensor according to the present invention for the detection of $NH_3$ or $NH_3$-containing gas mixtures is especially favorable. Use for detecting amine compounds or hydrazine is also conceivable. It is therefore likewise favorable to use a liquid electrolyte according to the present invention for detecting $NH_3$ or $NH_3$-containing gas mixtures. Use for detecting amine compounds or hydrazine is, of course, also conceivable here. The use of an electrochemical gas sensor according to the present invention, which contains a liquid electrolyte according to the present invention, for detecting $NH_3$, or $NH_3$-containing gas mixtures, amine compounds and/or hydrazine is also especially preferred in this connection.

Further features, details and specifics appear from the figures and exemplary embodiments described below. It is apparent that these exemplary embodiments are only exemplary and that further variants and exemplary embodiments will appear without problems for the person skilled in the art. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2a is a schematic side view of another exemplary embodiment of a gas sensor according to the present invention;

FIG. 2b is a top view of the separating element of the gas sensor from FIG. 2a along section line A-A;

DESCRIPTION OF THE PREFERRED EMBODIMENTS

Figure 1:
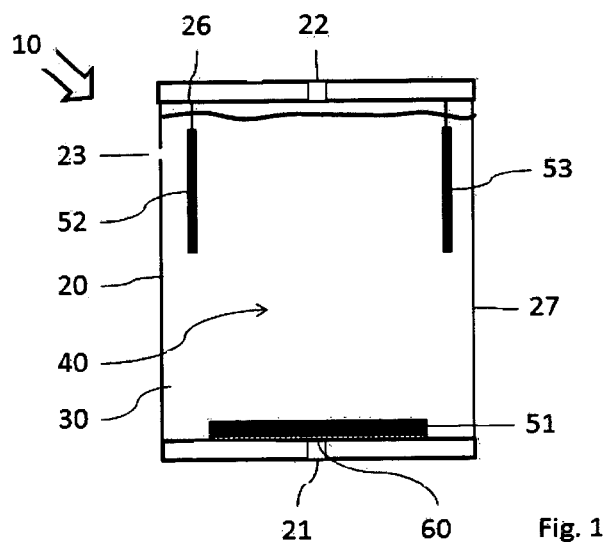
FIG. 1 is a schematic side view of an electrochemical gas sensor according to the present invention.

FIG. 1 shows an especially simple design of an electrochemical gas sensor 10 according to the present invention. The gas sensor 10 has a housing 20 with a gas inlet 21 and a gas outlet 22. The housing 20 has, furthermore, an additional opening 23, which is used for pressure equalization. The interior of the housing 20 is configured as an electrolyte reservoir 30. A working electrode 51, a counterelectrode 52 and a reference electrode 53 are arranged in the housing 20.

The working electrode 51 is arranged behind the gas inlet 21, so that it can react with gas flowing in, which contains reactive species. A protective membrane 60 is arranged between the working electrode 51 and the housing 20 in the area of the gas inlet 21.

The counterelectrode 52 is suspended on a counterelectrode carrier 26. The counterelectrode carrier 26 is fastened to the housing 20 in this exemplary embodiment. It is seen that electrolyte 40 flows around the counterelectrode 52 on all sides.

In this exemplary embodiment, the electrolyte 40 is a composition comprising a solvent, a conductive salt, an organic mediator and a buffer. The electrolyte is, for example, a composition comprising a solvent, which is a mixture of propylene carbonate and ethylene carbonate, 1-hexyl-3-methylimidazolium-tris(pentafluoroethyl)trifluorophosphate as the conductive salt, tert-butyl-1,2-dihydroxybenzene or anthraquinone-2-sulfonic acid as an organic mediator, as well as 3-(N-morpholino)-propanesulfonic acid as a buffer.

The gas sensor 10 according to the present invention shown in FIG. 2a also has a housing 20 with a gas inlet 21, a gas outlet 22 and an additional opening 23. A separating element 70, which divides the interior of the housing 20 into a lower chamber 24 and an upper chamber 25, is arranged in the housing 20 in this exemplary embodiment. The counterelectrode 52 is fastened, as in the exemplary embodiment already described in FIG. 1, to a counterelectrode carrier 26 and is located in the upper chamber 25. The reference electrode 53 is also arranged in the upper chamber 25.

The separating element 70 comprises a top part 71 and a foot part 72. The top part 71 is tubular and has an upper opening 73 and a lower opening (not shown in FIG. 2a), which corresponds to an opening of the foot part 72 (likewise not shown in FIG. 2a). The lower opening of the top part 71 may correspond to the opening of the foot part 72. The foot part 72 extends up to the housing wall 27 of the housing 20. In this way, the foot part 72 forms the separation between the upper and lower chambers 24, 25. The upper chamber 25 forms the electrolyte reservoir 30. The electrolyte 40 can reach the separating element 70 from the electrolyte reservoir 30 through the upper opening 73 of the top part 71 and flow from there through the foot part 72 into the lower chamber 24 of the housing.

The working electrode 51 and a collecting electrode 54 are arranged in the lower chamber 24. The working electrode 51 is arranged, just as in the exemplary embodiment shown in FIG. 1, behind the gas inlet 21 of the housing 20 in such a way that gas flowing in will reach the working electrode 51 as directly as possible. Only one protective membrane 60 is formed between the gas inlet 21 and the working electrode 51. This protective membrane 60 protects the working electrode 51 from mechanical damage, which may occur, for example, due to dust particles. It is seen that electrolyte 40 flowing into the lower chamber 24 flows around the working electrode 51 on all sides.

An intermediate membrane 61 is arranged between the working electrode 51 and the collecting electrode 54. This intermediate membrane 61 has such a dimensional stability that it prevents a direct contact between the working electrode 51 and the collecting electrode 54. At the same time, the intermediate membrane 61 is impregnated with the electrolyte 40. The working electrode 51 and the collecting electrode 54 are in a fluid contact with one another in this way.

An intermediate membrane 62 is also arranged between the collecting electrode 54 and the foot part 72 of the separating element 70. This second intermediate membrane 62 is also impregnated with the electrolyte 40. It is seen that the electrolyte 40 flow or can flow in this way from the upper chamber 25 through the separating element 70 and through the intermediate membrane 62 into the lower chamber 24. This also appears clearly especially in the cross section shown in FIG. 2b along line A-A from FIG. 2a. A top view of the separating element 70 arranged in the housing 20 is seen in this cross section. The foot part 72 of the separating element 70 has the shape of a disk. It extends up to the housing wall 27. The top part 71 of the separating element 70 has the shape of a tube with an upper opening 73 and with a lower opening 74. The lower opening 74 corresponds to an opening in the foot part 72. The top part 71 and the foot part 72 may be made in one piece, for example, as a continuous injection-molded or turned part, so that the lower opening of the top part 71 is at the same time the opening of the foot part 72. The view in FIG. 2b is a top view of the separating element 70 in direction B, which is shown in FIG. 2a. The intermediate membrane 62, which is arranged in the lower chamber 24, is viewed through the top part 71.

In another exemplary embodiment (not shown), only a working electrode 51 but no collecting electrode 54 may be arranged in a gas sensor 10, which is designed basically like the gas sensor 10 described in FIGS. 2a and 2b, in the lower chamber 24 instead of the combination of the working electrode 51, the collecting electrode 54 as well as the first and second intermediate membranes 61, 62. The first intermediate membrane 61 is arranged in this case directly between the working electrode 51 and the foot part 72 of the separating element 70.

Figures 3A, 3B:
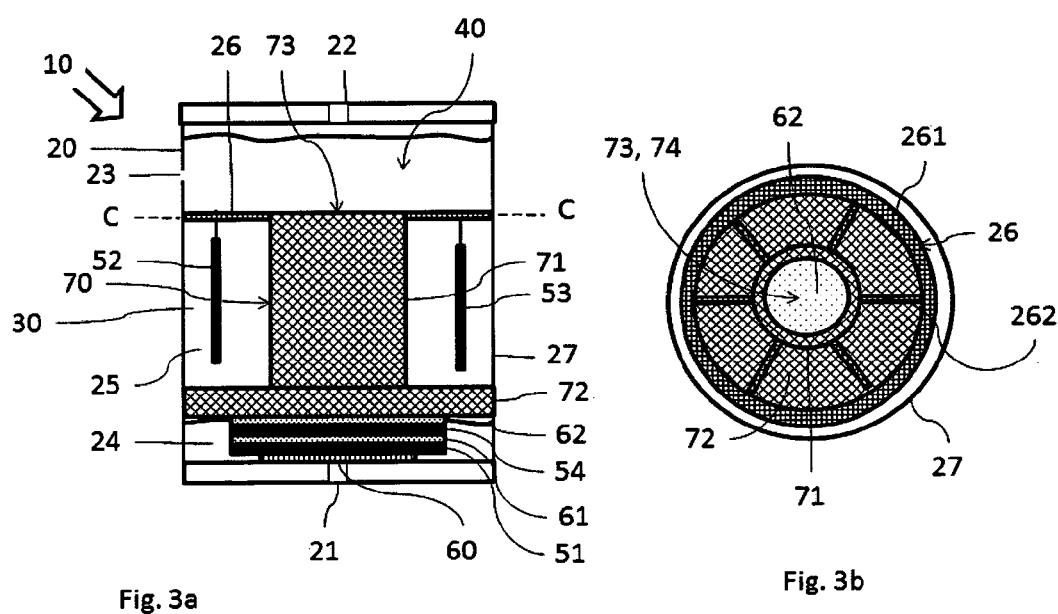
FIG. 3a is a schematic side view of another exemplary embodiment of a gas sensor according to the present invention.
FIG. 3b is a top view of the separating element of the gas sensor from FIG. 2b along section line C-C.

FIGS. 3a and 3b show another embodiment variant of the separating element 70. As in the exemplary embodiments described above, the gas sensor 10 has a housing 20 with a gas inlet 21, a gas outlet 22, an additional opening 23 and an electrolyte reservoir 30 here as well. The separating element 70 likewise divides the housing 20 into an upper and lower chamber 24, 25. The electrolyte reservoir 30 is formed by the upper chamber 25 in this case as well. The working electrode 51, a collecting electrode 54, as well as a first and a second intermediate membrane 61, 62 and a protective membrane 60 are arranged in the lower chamber, just as in the exemplary embodiment already described in FIG. 2a. To avoid repetitions, the statements made above will therefore be referred to at this point.

The counterelectrode carrier 26 is part of the separating element 70 in the exemplary embodiment shown in FIGS. 3a and 3b. It is seen that the counterelectrode 52 is fastened to this counterelectrode carrier 26 and is arranged in the upper chamber 25. The counterelectrode carrier 26 is formed by at least one spoke 261, which extends radially from the top part 71 of the separating element 70 to the housing wall 27 of the gas sensor 10. In the example being shown, the counterelectrode carrier 26 has an outer ring 262, which surrounds the top part 71 in the manner of a car wheel. The spokes 261 extend from the top part 71 to the ring 262. However, it is also conceivable in simpler, alternative exemplary embodiments (not shown) that one or more of the spokes 261 is/are in direct contact with the housing wall 27, without such a ring 262 being present.

The structure of the counterelectrode carrier 26 is seen especially well in the top view shown in FIG. 3b, which corresponds to a cross section along line C-C in FIG. 3a. The view is in the direction B (cf. FIG. 2a) from top to the separating element 70 arranged in the gas sensor 10.

The electrolyte 40 according to the present invention is present in the electrolyte reservoir 30 in each of the exemplary embodiments described. The electrolyte 40 can reach both the working electrode 51 and the collecting electrode 54. If the reactive species is $NH_3$, as in the example shown in FIG. 4, a chemical reaction can take place between the $NH_3$ flowing in, the material of the working and collecting electrodes 51, 54 and the electrolyte 40.

Figure 4:
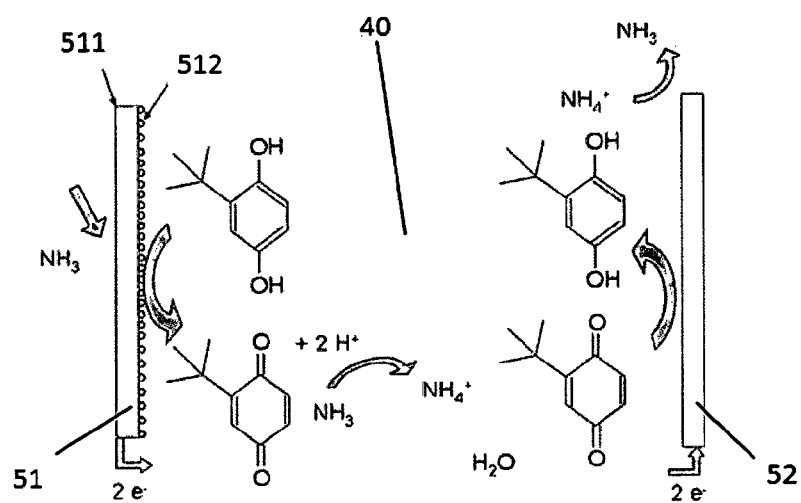
FIG. 4 is a schematic view showing a course of a detection reaction for $NH_3$ in an electrochemical gas sensor, which contains an electrolyte according to the present invention.

$NH_3$ flowing into the gas sensor 10 now reacts on the surface of the working electrode 51 with the electrolyte. The working electrode 51 preferably consists, e.g., of a PTFE membrane 511 with a carbon nanotubes coating 512. The counterelectrode 52 preferably consists of a noble metal. The electrolyte 40 is a composition comprising propylene carbonate and/or ethylene carbonate as the solvent, 1-hexyl-3-methyl-imidazolium-tris(pentafluoroethyl)-trifluorophosphate as the conductive salt and tert-butyl-1,2-dihydroxybenzene as the organic mediator in this example. The electrolyte preferably contains, furthermore, a buffer, namely, 3-(N-morpholino)-propanesulfonic acid. As can be seen in FIG. 4, the tert-butyl-1,2-dihydroxybenzene is oxidized into tert-butylquinone at the working electrode 51. The protons released in the process react with the $NH_3$ flowing into the gas sensor 10 into ammonium ions. The ammonium ions reach the counterelectrode 52, where the reverse reaction of the tert-butylquinone formed previously into 1,2-dihydroxybenzene takes place. $NH_3$, which can escape through the gas outlet 22, is released, in turn from the ammonium ions. The buffer used stabilizes the pH value of the electrolyte, which is present between the working electrode and the counterelectrode 51, 52 in the electrolyte reservoir 30, in the course of this reaction process.

It is seen on the basis of FIG. 4 that an electrolyte 40 can be used for detecting nitrogen-containing compounds, especially $NH_3$. The electrolyte 40 is filled into the electrolyte reservoir 30, for example, in a gas sensor 10 corresponding to one of the exemplary embodiments, which are shown in FIG. 1, 2a, 2b, 3a or 3b. In other words, an electrochemical gas sensor 10, as it is shown in FIGS. 1, 2a, 2b, 3a, 3b, can be used to detect nitrogen-containing compounds, e.g., $NH_3$, amine compounds and/or hydrazine, especially if the above-described electrolyte 40 is filled in its electrolyte reservoir 30. It is obvious that the electrolyte 40 is not limited to the example described in reference to FIG. 1, but the electrolyte 40 may have any composition according to the present invention, as it is described above.

All the features and advantages, including design details, arrangements in space and method steps, which are highlighted in the description and in the drawings, may be essential for the present invention both in themselves and in the various combinations.

While specific embodiments of the invention have been shown and described in detail to illustrate the application of the principles of the invention, it will be understood that the invention may be embodied otherwise without departing from such principles.

What is claimed is:

1. A liquid electrolyte for an electrochemical gas sensor comprising a housing, a working electrode, a counterelectrode, a reference electrode, wherein the housing has an electrolyte reservoir, a gas inlet opening and at least one gas outlet opening, a liquid electrolyte in the electrolyte reservoir and a counterelectrode carrier, the counterelectrode being suspended on the counterelectrode carrier such that the counterelectrode is suspended in the electrolyte reservoir and the electrolyte flows around the counterelectrode on all sides, wherein the electrolyte contains at least one conductive salt, a solvent and an organic mediator, wherein the electrolyte contains, furthermore, a buffer, said buffer being a compound according to

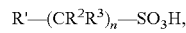

Formula I in which one of:
n=1, 2, 3, 4 or 5, preferably n=2 or n=3, wherein $R^2$ and $R^3$ are selected, independently from one another, from among H, NH and OH, and wherein R' is selected from the group containing piperazinyl, substituted piperazinyl, N-morpholino, cycloalkyl, tris-(hydroxyalkyl)alkyl; and
n=2 or n=3, wherein all $R^2$ and $R^3$ are selected, independently from one another, from among H, NH and OH, and wherein R' is selected from the group containing [4-(2-hydroxyethyl)-1]-piperazinyl, (N-morpholino)-, N-cyclohexyl-, tris-(hydroxymethyl)methyl, wherein the conductive salt contains an ionic liquid and wherein the solvent is selected from among water, propylene carbonate, ethylene carbonate or mixtures thereof.

2. An electrolyte according to claim 1, wherein the organic mediator is selected from the group containing ortho-quinones, para-quinones, substituted ortho-quinones and substituted para-quinones, dihydroxynaphthalene, substituted dihydroxynaphthalene, anthraquinone, and substituted anthraquinone, 1,2-dihydroxybenzene, 1,4-dihydroxybenzene, 1,4-naphthodihydroxybenzene, substituted 1,2-dihydroxybenzene, substituted 1,4-dihydroxybenzene, and substituted 1,4-naphthodihydroxybenzene, substituted anthraquinone, substituted 1,2-dihydroxybenzene, and substituted 1,4-dihydroxybenzene, wherein the substituents of the substituted anthraquinones, substituted 1,2-dihydroxybenzene and/or substituted 1,4-hydroquinone are selected from the group containing sulfonyl, tert-butyl, hydroxyl, alkyl, aryl, preferably sulfonic acid, and tert-butyl.

3. An electrolyte according to claim 1, wherein the buffer is 3-(N-morpholino)-propanesulfonic acid.

4. An electrochemical gas sensor method comprising the steps of:
providing an electrochemical gas sensor comprising a housing, a working electrode, a counterelectrode, a reference electrode, wherein the housing has an electrolyte reservoir, a gas inlet opening and at least one gas outlet opening and a counterelectrode carrier, the counterelectrode being suspended on the counterelectrode carrier such that the counterelectrode is suspended in the electrolyte reservoir; and
providing a liquid electrolyte in the electrolyte reservoir, wherein the electrolyte contains at least one conductive salt, a solvent and an organic mediator and the counterelectrode is completely submerged in the electrolyte, wherein the electrolyte flows around the counterelectrode on all sides.

5. An electrochemical gas sensor method according to claim 4, further comprising detecting $NH_3$ or $NH_3$-containing gas mixtures with the electrochemical gas sensor with the provided liquid electrolyte.

6. An electrochemical gas sensor method according to claim 4, wherein the electrolyte contains a buffer comprised of a compound according to

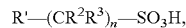

Formula I in which one of:
- n=1, 2, 3, 4 or 5, preferably n=2 or n=3, wherein $R^2$ and $R^3$ are selected, independently from one another, from among H, NH and OH, and wherein R' is selected from the group containing piperazinyl, substituted piperazinyl, N-morpholino, cycloalkyl, tris-(hydroxyalkyl)alkyl; and
- n=2 or n=3, wherein all $R^2$ and $R^3$ are selected, independently from one another, from among H, NH and OH, and wherein R' is selected from the group containing [4-(2-hydroxyethyl)-1]-piperazinyl, (N-morpholino)-, N-cyclohexyl-, tris-(hydroxymethyl)methyl, wherein the conductive salt contains an ionic liquid and wherein the solvent is selected from among water, propylene carbonate, ethylene carbonate or mixtures thereof.

7. An electrochemical gas sensor method according to claim 4, wherein the electrochemical gas sensor comprises a separating element, the counterelectrode carrier comprising a radial spoke extending between the separating element and the housing, the counterelectrode being suspended on the radial spoke such that the counterelectrode is suspended in the electrolyte reservoir and the electrolyte flows around the counterelectrode on all sides of the counterelectrode.

8. An electrochemical sensor comprising:
- a housing;
- a working electrode;
- a counterelectrode;
- a reference electrode, wherein the housing has an electrolyte reservoir, a gas inlet opening and at least one gas outlet opening;
- a liquid electrolyte in the electrolyte reservoir; and
- a counterelectrode carrier, the counterelectrode being suspended on the counterelectrode carrier such that the counterelectrode is suspended in the electrolyte reservoir and the electrolyte flows around the counterelectrode on all sides, wherein the electrolyte contains at least one conductive salt, a solvent and an organic mediator, wherein the electrolyte contains, furthermore, a buffer, said buffer being a compound according to $$R'-(CR^2R_3)_n-SO_3H, \quad \text{Formula I}$$

in which one of:
- n=1, 2, 3, 4 or 5, preferably n=2 or n=3, wherein $R^2$ and $R^3$ are selected, independently from one another, from among H, NH and OH, and wherein R' is selected from the group containing piperazinyl, substituted piperazinyl, N-morpholino, cycloalkyl, tris-(hydroxyalkyl)alkyl; and
- n=2 or n=3, wherein all $R^2$ and $R^3$ are selected, independently from one another, from among H, NH and OH, and wherein R' is selected from the group containing [4-(2-hydroxyethyl)-1]-piperazinyl, (N-morpholino)-, N-cyclohexyl-, tris-(hydroxymethyl)methyl, wherein the conductive salt contains an ionic liquid and wherein the solvent is selected from among water, propylene carbonate, ethylene carbonate or mixtures thereof.

9. An electrochemical sensor according to claim 8, wherein the organic mediator is selected from the group containing ortho-quinones, para-quinones, substituted ortho-quinones and substituted para-quinones, dihydroxynaphthalene, substituted dihydroxynaphthalene, anthraquinone, and substituted anthraquinone, 1,2-dihydroxybenzene, 1,4-dihydroxybenzene, 1,4-naphthodihydroxybenzene, substituted 1,2-dihydroxybenzene, substituted 1,4-dihydroxybenzene, and substituted 1,4-naphthodihydroxybenzene, substituted anthraquinone, substituted 1,2-dihydroxybenzene, and substituted 1,4-dihydroxybenzene, wherein the substituents of the substituted anthraquinones, substituted 1,2-dihydroxybenzene and/or substituted 1,4-hydroquinone are selected from the group containing sulfonyl, tert-butyl, hydroxyl, alkyl, aryl, preferably sulfonic acid, and tert-butyl.

10. An electrochemical sensor according to claim 8, wherein the buffer is 3-(N-morpholino)-propanesulfonic acid.

11. An electrochemical sensor according to claim 8, further comprising:
- a separating element, the counterelectrode carrier comprising a radial spoke extending between the separating element and the housing, the counterelectrode being suspended on the radial spoke such that the counterelectrode is suspended in the electrolyte reservoir and the electrolyte flows around the counterelectrode on all sides.

12. An electrochemical sensor according to claim 11, wherein the separating element divides the housing into an upper chamber and a lower chamber.

13. An electrochemical sensor according to claim 12, wherein the upper chamber forms the electrolyte reservoir.

14. An electrochemical sensor according to claim 12, wherein the working electrode is arranged in the lower chamber.

15. An electrochemical sensor according to claim 12, wherein the separating element is configured to guide electrolyte through the separating element from the upper chamber into the lower chamber.

16. An electrochemical sensor according to claim 12, wherein the separating element has at least one top part and one foot part.

17. An electrochemical sensor according to claim 12, wherein the counterelectrode carrier is part of the separating element.

18. An electrochemical sensor according to claim 8, further comprising a collecting electrode, the housing comprising a bottom housing portion, the reference electrode being located at a spaced location from the counterelectrode, the reference electrode extending downward from another radial spoke of the counterelectrode carrier in a direction of the bottom housing portion.

* * * * *